United States Patent [19]
Synenki et al.

[11] Patent Number: 5,849,694
[45] Date of Patent: Dec. 15, 1998

[54] STABLE AND BIOACTIVE MODIFIED PORCINE SOMATOTROPIN AND PHARMACEUTICAL COMPOSITIONS THEREOF

[76] Inventors: Richard M. Synenki; Peter M. Rubinelli; Henry E. Auer; James E. Seely, all of P.O. Box 207, Terre Haute, Ind. 47808

[21] Appl. No.: 553,511

[22] Filed: Jul. 16, 1990

[51] Int. Cl.⁶ .......................... A61K 38/27; C07K 14/61; C12N 15/18
[52] U.S. Cl. ............................ 514/12; 530/399; 930/120; 435/69.4
[58] Field of Search ................................ 530/399; 514/12; 435/69.4; 930/120

[56] References Cited

U.S. PATENT DOCUMENTS

| | | | |
|---|---|---|---|
| 3,853,832 | 12/1974 | Li | 530/399 |
| 4,443,539 | 4/1984 | Frazier et al. | 435/68 |
| 4,518,584 | 5/1985 | Mark et al. | 424/85 |
| 4,588,585 | 5/1986 | Mark et al. | 424/85 |
| 4,604,359 | 8/1986 | Goeddel et al. | 435/253 |
| 4,656,255 | 4/1987 | Seely | 530/412 |
| 4,737,462 | 4/1988 | Mark et al. | 435/253 |
| 4,742,003 | 5/1988 | Derynck et al. | 435/68 |
| 5,079,230 | 1/1992 | Randawa et al. | 530/399 |

FOREIGN PATENT DOCUMENTS

| | | |
|---|---|---|
| 4020289 | 3/1990 | Australia . |
| 104920 | 4/1984 | European Pat. Off. . |
| 8905445 | 8/1990 | WIPO . |

OTHER PUBLICATIONS

Tokunaga et al *Eur J. Biochem* 153:445 (1985).
Brems et al. *J. of Biological Chem* 265(10):5504(1990).
Abdel–Megvid et al. *Proc Natl Acad Sci USA* 84:6434(1987).
Kunkel et al., "Methods in Enzymology" 154: 367–82 (1987).

*Primary Examiner*—John Ulm
*Assistant Examiner*—Christine Saoud

[57] ABSTRACT

The present invention provides a stable and bioactive recombinant small-loop modified somatotropin which has its small-loop cysteines changed to other amino acids or deleted altogether and a method for producing such a small-loop modified somatotropin. Also provided by the present invention are DNA sequences coding for such small-loop modified somatotropins, plasmids containing such sequences, and organisms containing such plasmids. Furthermore, pharmaceutical compositions including small-loop modified somatotropins and methods for using such pharmaceutical compositions are disclosed.

4 Claims, 7 Drawing Sheets

FIG. 1

```
1               5
TTC CCA GCC ATG CCC TTG TCC
Phe Pro Ala Met Pro Leu Ser 10              15                  20
AGC TTG TTT GCC AAC GCT GTG CTC CGG GCC CAG CAC CTG CAC
Ser Leu Phe Ala Asn Ala Val Leu Arg Ala Gln His Leu His 25              30                  35
CAA CTG GCT GCT GAC ACC TAC AAG GAG TTT GAG CGC GCC TAC ATC
Gln Leu Ala Ala Asp Thr Tyr Lys Glu Phe Glu Arg Ala Tyr Ile 40              45                  50
CCG GAG GGA CAG AGG TAC TCC ATC CAG ACC GCC CAG GCT GCC TTC
Pro Glu Gly Gln Arg Tyr Ser Ile Gln Thr Ala Gln Ala Ala Phe 55              60                  65
TGC TTC TCG GAG ACC ATC CCG GCC CCC ACG GGC AAG GAC GAG GCC
Cys Phe Ser Glu Thr Ile Pro Ala Pro Thr Gly Lys Asp Glu Ala 70              75                  80
CAG CAG AGA TCG GAC GTG GAG CTG CTG CGC TTC TCG CTG CTC CTC
Gln Gln Arg Ser Asp Val Glu Leu Leu Arg Phe Ser Leu Leu Leu 85              90                  95
ATC CAG TCG TGG CTC GGG CCC GTG CAG TTC CTC AGC AGG GTC TTC
Ile Gln Ser Trp Leu Gly Pro Val Gln Phe Leu Ser Arg Val Phe 100             105                 110
ACC AAC AGC CTG GTG TTT GGC ACC TCA GAC CGC GTC TAC GAG AAG
Thr Asn Ser Leu Val Phe Gly Thr Ser Asp Arg Val Tyr Glu Lys 115             120                 125
CTG AAG GAC CTG GAG GAG GGC ATC CAG GCC CTG ATG CGG GAG CTG
Leu Lys Asp Leu Glu Glu Gly Ile Gln Ala Leu Met Arg Glu Leu 130             135                 140
GAG GAT GGC AGC CCC CGG GCA GGA CAG ATC CTC AAG CAA ACC TAC
Glu Asp Gly Ser Pro Arg Ala Gly Gln Ile Leu Lys Gln Thr Tyr 145             150                 155
GAC AAA TTT GAC ACA AAC TTG CGC AGT GAT GAC GCG CTG CTT AAG
Asp Lys Phe Asp Thr Asn Leu Arg Ser Asp Asp Ala Leu Leu Lys 160             165                 170
AAC TAC GGG CTG CTC TCC TGC TTC AAG AAG GAC CTG CAC AAG GCT
Asn Tyr Gly Leu Leu Ser Cys Phe Lys Lys Asp Leu His Lys Ala 175             180                 185
GAG ACA TAC CTG CGG GTC ATG AAG TGT CGC CGC TTC GTG GAG AGC
Glu Thr Tyr Leu Arg Val Met Lys Cys Arg Arg Phe Val Glu Ser

190
AGC TGT GCC TTC
Ser Cys Ala Phe
```

FIG. 2

```
1                   5                   10
AGC TTG TTT GCC AAC GCT GTG CTC CGG GCC CAG CAC CTG CAC
Ser Leu Phe Ala Asn Ala Val Leu Arg Ala Gln His Leu His 15                  20                  25
CAA CTG GCT GCT GAC ACC TAC AAG GAG TTT GAG CGC GCC TAC ATC
Gln Leu Ala Ala Asp Thr Tyr Lys Glu Phe Glu Arg Ala Tyr Ile 30                  35                  40
CCG GAG GGA CAG AGG TAC TCC ATC CAG ACC GCC CAG GCT GCC TTC
Pro Glu Gly Gln Arg Tyr Ser Ile Gln Thr Ala Gln Ala Ala Phe 45                  50                  55
TGC TTC TCG GAG ACC ATC CCG GCC CCC ACG GGC AAG GAC GAG GCC
Cys Phe Ser Glu Thr Ile Pro Ala Pro Thr Gly Lys Asp Glu Ala 60                  65                  70
CAG CAG AGA TCG GAC GTG GAG CTG CTG CGC TTC TCG CTG CTG CTC
Gln Gln Arg Ser Asp Val Glu Leu Leu Arg Phe Ser Leu Leu Leu 75                  80                  85
ATC CAG TCG TGG CTC GGG CCC GTG CAG TTC CTC AGC AGG GTC TTC
Ile Gln Ser Trp Leu Gly Pro Val Gln Phe Leu Ser Arg Val Phe 90                  95                  100
ACC AAC AGC CTG GTG TTT GGC ACC TCA GAC CGC GTC TAC GAG AAG
Thr Asn Ser Leu Val Phe Gly Thr Ser Asp Arg Val Tyr Glu Lys 105                 110                 115
CTG AAG GAC CTG GAG GAG GGC ATC CAG GCC CTG ATG CGG GAG CTG
Leu Lys Asp Leu Glu Glu Gly Ile Gln Ala Leu Met Arg Glu Leu 120                 125                 130
GAG GAT GGC AGC CCC CGG GCA GGA CAG ATC CTC AAG CAA ACC TAC
Glu Asp Gly Ser Pro Arg Ala Gly Gln Ile Leu Lys Gln Thr Tyr 135                 140                 145
GAC AAA TTT GAC ACA AAC TTG CGC AGT GAT GAC GCG CTG CTT AAG
Asp Lys Phe Asp Thr Asn Leu Arg Ser Asp Asp Ala Leu Leu Lys 150                 155                 160
AAC TAC GGG CTG CTC TCC TGC TTC AAG AAG GAC CTG CAC AAG GCT
Asn Tyr Gly Leu Leu Ser Cys Phe Lys Lys Asp Leu His Lys Ala 165                 170                 175
GAG ACA TAC CTG CGG GTC ATG AAG TGT CGC CGC TTC GTG GAG AGC
Glu Thr Tyr Leu Arg Val Met Lys Cys Arg Arg Phe Val Glu Ser

180
AGC TGT GCC TTC
Ser Cys Ala Phe
```

FIG. 3

```
163                          170
AAG GCT GAG ACA TAC CTG GGG GTC
Lys Ala Glu Thr Tyr Leu Arg Val

175
ATG AAG AAC CGC CGC TTC GTG GAG
Met Lys Asn Arg Arg Phe Val Glu

180
AGC AGC AGC GCC TTC
Ser Ser Ser Ala Phe
```

FIG. 4

```
        165
AAG GCT GAG ACA TAC CTG GCG
Lys Ala Glu Thr Tyr Leu Arg 170                 175
GTC ATG AAG GCG CGC CGC TTC
Val Met Lys Ala Arg Arg Phe

180
GTG GAG AGC AGC GCG GCC TTC
Val Glu Ser Ser Ala Ala Phe
```

STABLE AND BIOACTIVE MODIFIED PORCINE SOMATOTROPIN AND PHARMACEUTICAL COMPOSITIONS THEREOF

FIELD OF THE INVENTION

This invention relates generally to somatotropins and particularly to stable and bioactive recombinantly modified somatotropins, DNA sequences coding for the modified somatotropins, plasmids containing DNA sequences coding for the modified somatotropins, and transformed microorganisms with DNA sequences coding for the modified somatotropins. Additionally, processes for constructing the novel DNA sequences, plasmids and microorganisms are disclosed. Pharmaceutical compositions including the modified somatotropins and methods of using the pharmaceutical compositions also are disclosed.

BACKGROUND OF THE INVENTION

The isolation, purification and properties of somatotropins are well known in the art. Somatotropin, a protein sometimes referred to as growth hormone, is produced by an animal's pituitary gland throughout the animal's life. Somatotropin promotes skeletal growth, nitrogen retention, protein synthesis and affects glucose and lipid metabolism. Accordingly, somatotropin is recognized as a general anabolic agent.

Somatotropin can be isolated from excised pituitary tissue. See, e.g., Li, *J. Biol. Chem.*, 211:55 (1954). Somatotropin also can be obtained from genetically engineered microorganisms containing recombinant DNA which specifies the production of somatotropin. See, e.g., Seeburg, et al., *Nature*, 276:795–798 (1978); Seeburg, et al., *Nature*, 270:486–494 (1978); Martial, *Science*, 205:602–607 (1979); and Seeburg, et al., *DNA*, 2:37–45 (1983). Throughout this specification, including the example, the cited references are incorporated herein by reference.

Somatotropins from a variety of species have been studied and characterized. For example, bovine somatotropin is known to be synthesized in, and secreted from, the anterior lobe of the cow's pituitary. A nucleotide coding sequence and an amino acid sequence of native bovine somatotropin have been reported, e.g. Miller et al., *J. Biol. Chem.*, 255:7521–24 (1980); and Wallis, *FEBS Lett*, 35:11–14 (1973). Bovine somatotropin also has been produced via recombinant DNA technology in appropriate hosts, e.g. Miller et al., *J. Biol. Chem.*, 255:7521–24 (1980). U.S. Pat. No. 4,443,539 to Frazier et al. discloses a process for preparing bovine somatotropin by utilizing recombinant DNA methodology to place the bovine somatotropin structural gene into yeast cells. U.S. Pat. No. 4,371,462 to Hecht, discloses a method for the purification of anterior pituitary peptides. European Patent Application Nos. 83304574.3, filed Aug. 8, 1983, with Publication Number 103,395; 82304880.6, filed Sep. 16, 1982, with Publication Number 075,444; and 81303824.7, filed Aug. 21, 1981, with Publication Number 047,600; and British Patent Application No. 2,073,245A disclose methods for producing recombinant bovine somatotropin in high yields. Strains of *E. coli* that produce bovine somatotropin are available from the American Type Culture Collection under accession numbers ATCC 31826, 31840, 31841, 31842, and 31843.

Similarly, the preparation of natural and recombinant porcine and human somatotropin is well known. For example, in addition to the publications above, U.S. Pat. No. 4,604,359 discloses methods for the microbial expression of human somatotropin; U.S. Pat. No. 4,332,717 discloses methods for the purification of human somatotropin; and European Patent Application No. 83305717.7, filed Sep. 26, 1983, with Publication Number 104,920, discloses methods for producing recombinant porcine somatotropin in high yields. U.S. Pat. No. 4,604,359 discloses methods for synthesizing bioactive human somatotropin, including methods for synthesizing a bioactive tetra-S-carbamidomethyl derivative. Many other such publications and methods for obtaining various somatotropins are well known to skilled artisans, e.g., U.S. Pat. No. 4,645,755 discloses methods for producing fish somatotropin.

Somatotropins isolated from different species of animals have a high degree of amino acid sequence homology, differing slightly in the number and the sequence of amino acids present in the peptide chain. For example, native human somatotropin (nhST) is a polypeptide constructed from 188 amino acids, four of which are cysteines located at positions 68, 162, 179 and 186. The cysteines form two disulfide bonds; (cystine bonds) one between amino acids 179 and 186 and one between amino acids 68 and 162. The segment of amino acids between amino acid 179 and 186 forms what is known in the art as a "small loop." The complete sequence and structure of human somatotropin, illustrating the "small-loop" and "large-loop," are presented in U.S. Pat. No. 3,853,832, incorporated herein by reference.

Native porcine somatotropin (npST) is a 190 amino acid polypeptide having two cystine bonds forming the characteristic small-loop and large-loop. The small loop is formed of the amino acids between the cysteines at positions 180 and 188 and the large loop between amino acids 163 and 52. Native bovine somatotropin (nbST) is a 191 amino acid polypeptide also having two cystine bonds forming the characteristic small-loop and large-loop. Here, the small loop is between cysteines at positions 181 and 189 and the large loop of the amino acids is between cysteines at positions 53 and 164. All native somatotropins appear to have a characteristic tertiary conformation having the above-described small and large loops. Although recombinant or synthetic somatotropins can have varying numbers or sequences of amino acids, all to this date appear to include the large and small loops.

European Patent Application Publication No. 0 103 395 describes the construction of a transformed strain of *E. coli* containing a first plasmid which codes for delta-9 (Ser) bovine somatotropin (somatotropin less its 9 N-terminal amino acids and having an additional serine residue at the N-terminus) under the control of the lambda $P_L$ promoter-operator and having a Shine-Delgarno region derived from bacteriophage mu (Pmu). This transformant contains a second plasmid, pcI857, which codes for the production of the cI857 temperature-sensitive repressor protein. This plasmid and the resultant protein are known to those of skill in the art. The repressor protein can be inactivated by raising the temperature to from about 37° to 42° C., thereby inducing expression of delta-9 (Ser) bovine somatotropin. A transformant strain of this type, *E. coli* HB101 ($P_L$mu-delta-9 (Ser) bovine somatotropin and pcI857) has been deposited with the American Type Culture Collection (ATCC) in Rockville, Md., and assigned Accession No. 53030.

Construction of a transformant strain which codes for the production of delta-7 porcine somatotropin (porcine somatotropin less its first 7 N-terminal amino acids) is described in European Patent Application Publication No. 0 104 920. A transformant strain capable of producing Δ7-porcine somatotropin, *E. coli* HB101 ($P_L$mu-delta-7 porcine somatotropin and cI857) has been deposited with ATCC and assigned Accession No. 53031.

Strains 53030 and 53031 are prolific producers of delta-9 (Ser) bovine somatotropin and delta-7 porcine somatotropin, respectively.

Although methods for producing somatotropins are well known, methods for storing somatotropin are not well developed. Somatotropins produced by the above-described techniques do not lend themselves to long-term storage although a long period of time may pass before the produced somatotropin actually is used. During this storage period it is known that somatotropins tend to form bio-inactive dimers, oligomers, and insoluble aggregates. These bio-inactive forms of the somatotropin lower the amount of somatotropin available for use and can cause problems during administration, particularly when insoluble aggregates form unusable precipitates.

Accordingly, somatotropins which are stable and remain bioactive during storage are needed. Such somatotropins must be resistant to the formation of bio-inactive dimers, oligomers and aggregates during storage.

It is, therefore, an object of the present invention to provide stable and bio-active modified somatotropins which do not tend to form bio-inactive dimers, oligomers, and aggregates during production and storage.

It is another object of the present invention to provide a method for producing such somatotropins.

It is a further object of the present invention to provide a pharmaceutical composition containing a stable and bioactive modified somatotropin which does not tend to form bio-inactive dimers, oligomers, or aggregates during storage. Additionally, the composition should be suitable for long-term storage and easy dosage preparation and administration.

It is another object of the present invention to provide a DNA sequence coding for a stable and bioactive modified somatotropin which does not form bioinactive dimers, oligomers, or aggregates during production and storage.

It is another object of the present invention to provide a plasmid containing such a DNA sequence and a microorganism transformed with such a plasmid.

SUMMARY OF THE INVENTION

The present invention provides recombinantly modified bioactive somatotropins which lack the small loop characteristic of the corresponding native polypeptides. Furthermore, the present invention provides DNA sequences coding for such modified somatotropins, plasmids containing such DNA sequences and recombinant microorganisms which have been transformed with such plasmids. Additionally, the present invention provides methods of constructing each of the above and pharmaceutical compositions containing somatotropins lacking the small loop. The present invention also provides methods of using the modified bioactive somatotropins to promote growth.

BRIEF DESCRIPTION OF THE DRAWINGS

FIG. 2 is the nucleic and amino acid sequence of delta 7 porcine somatotropin (Δ7pST).

DETAILED DESCRIPTION OF THE INVENTION

A. Definitions

The term "somatotropin" as used herein encompasses any somatotropin having a "large-loop" formed by disulfide bonds between cysteine residues of the protein and includes not only "native somatotropins" but also "synthetic somatotropins" and "recombinant somatotropins" capable of producing the physiological effects of native somatotropin when administered to animals or humans.

Native somatotropins are defined as somatotropins produced in vivo by animals.

Synthetic somatotropins are defined as chemically synthesized polypeptides which exhibit the growth promoting physiological effects of native somatotropins.

Recombinant somatotropins are polypeptide sequences, produced via recombinant genetic manipulations, which exhibit the growth promoting effects of native somatotropin. Such somatotropins can have the amino acid sequence of native somatotropin, amino acid sequences substantially similar thereto, or an abbreviated sequence thereof, and include analogs and muteins having substituted, deleted, elongated, replaced, or otherwise modified sequences. In particular, "somatotropin", as used herein, includes a recombinant protein of the same sequence as the native somatotropin, but having amino acids deleted from the amino and/or carboxy terminal end. Examples of such proteins include, but are not limited to, delta-7 recombinant porcine somatotropin, and delta-4 recombinant bovine somatotropin, having 7 and 4 residues deleted from the amino terminal end respectively.

The term "small-loop modified somatotropin" as used herein describes a "somatotropin" that has a large-loop, as previously described, but does not have a small-loop. The small loop is not present because the cysteines which provide the small-loop forming sulfhydryl groups have been replaced with other amino acids, thereby preventing the formation of the necessary cystine, or disulfide, bond. The small-loop modified somatotropin can be identical in amino acid sequence to a non-modified "somatotropin" with the exception that the cysteines typically involved in small-loop formation in native somatotropins have been replaced by other amino acids.

B. Description

The tertiary structure of a genetically engineered porcine somatotropin is illustrated in Abdel-Meguid, et al., "Three-dimensional Structure of a Genetically Engineered Variant of Porcine Growth Hormone" *Proc. Natl. Acad., U.S.A.*, 84:6434–6437 (1987), incorporated herein by reference.

The present invention provides for a DNA sequence which codes for a small-loop modified somatotropin. Preferred types of somatotropins are porcine, bovine or human somatotropins. An especially preferred somatotropin is delta 7 porcine somatotropin (Δ7pST). The Δ7 indicates that 7 amino acids from the N-terminus of the polypeptide have been deleted. As previously disclosed, organisms capable of producing Δ7pST are available from the American Type Culture Collection at Rockville, Md.

The DNA sequence of the present invention can be produced by any suitable method, including chemical synthesis or recombinant techniques. An especially preferred technique is that of site-directed mutagenesis as disclosed in Kunkel et al., *Methods in Enzymology*, 154:367–382 (1987), incorporated herein by reference. In site-directed mutagenesis a small oligonucleotide which has a sequence that is complimentary to the bases on both sides of the codon coding for the amino acid to be changed is annealed to a single stranded DNA coding for a protein. A non-complementary 3-base pair sequence is opposite the codon coding for the amino acid to be changed, hereinafter referred to as the "substitution site". Generally, the oligonucleotide sequence can be from 15 to 30 bases in length. Longer oligonucleotides are more stable than shorter oligonucleotides, due to the increased number of correctly oriented hydrogen bonds between bases. It is preferred to have an equal number of complementary bases on each side of the substitution site. A codon coding for the amino acid to be substituted is inserted in the oligonucleotide and annealed to the parent single stranded DNA. After the oligonucleotide containing the codon for the amino acid which will substitute for the amino acid to be changed is annealed to the single stranded DNA, treatment with a DNA polymerase followed by T4 ligase, according to methods known to those of skill in the art, produces a double stranded DNA molecule. Selection for the strand of DNA coding for the protein having the amino acid substitution at the desired location is done according to the method of Kunkel et al. Repetition of the oligonucleotide hybridization can result in further specific amino acid substitutes in a polypeptide sequence.

In the present invention, the cysteines which form disulfide bridges resulting in a somatotropin having a small-loop in its tertiary structure can be substituted for by other amino acids using the technique of Kunkel et al. The resulting small-loop modified somatotropin does not have the cysteines which could cause a small loop to form in native somatotropin, yet the bioactivity is comparable with native somatotropins.

Expression of the small-loop modified somatotropin gene results in the production of somatotropins which cannot form intramolecular cystine bonds with the small loop cysteines. Accordingly, formation of dimers, oligomers and aggregates is greatly reduced during storage of the somatotropin. In turn, higher bioactivity per administered dose is achieved.

Figure 4:
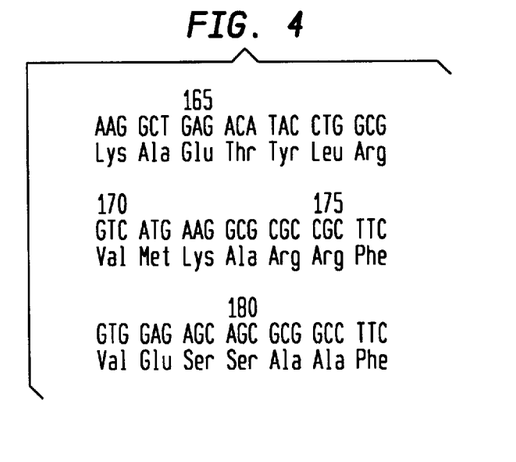
FIG. 4 is the nucleic and amino acid sequence of amino acids 163–183 of Δ7pST showing alanine at positions 173 and 181.
Figure 5A:
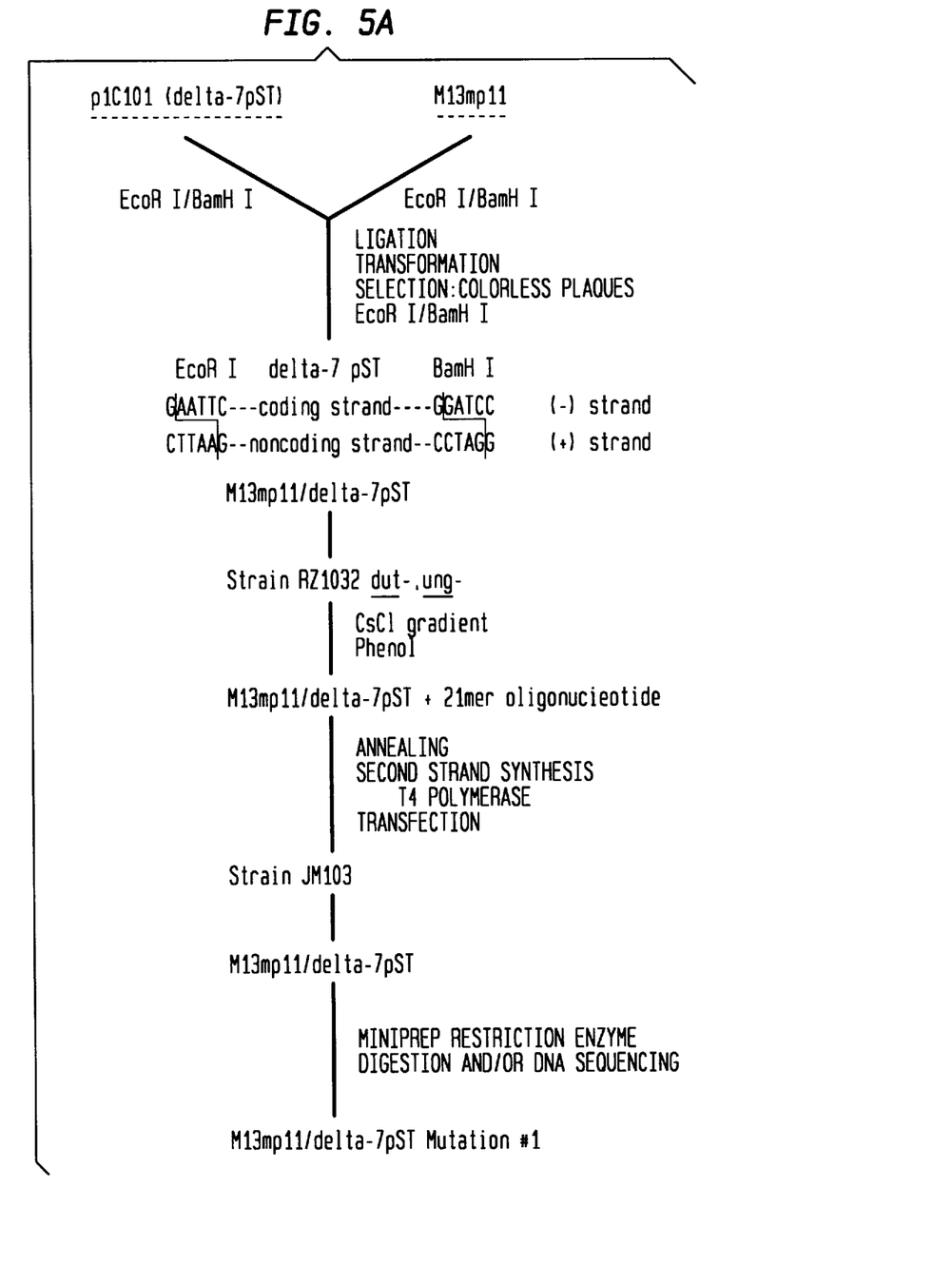
FIGS. 5A and 5B illustrate the process of site-directed mutagenesis.
Figure 5B:
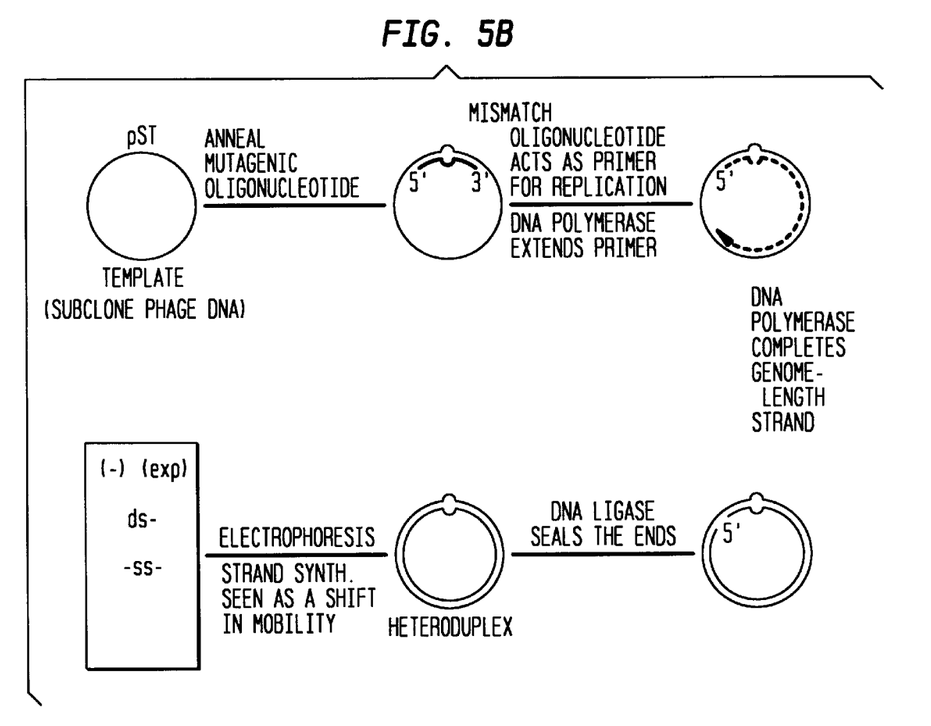
Figure 6:
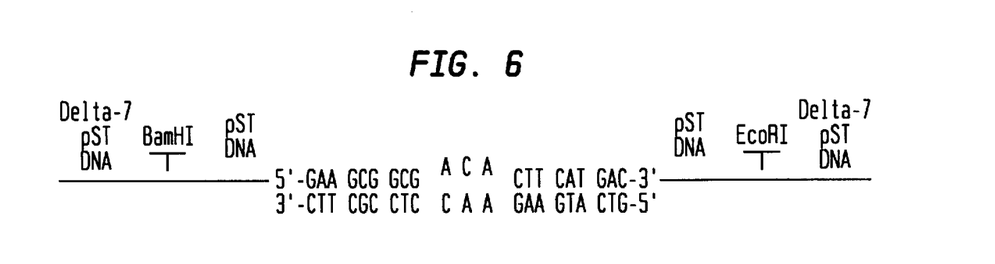
FIG. 6 shows an asparagine (173) oligonucleotide annealed to the Δ7pST DNA.

In one embodiment of the present invention as is illustrated in FIG. 4, the DNA sequence encoding Δ7pST has been modified by replacing the codons encoding cysteine at positions 173 and 181 of the peptide sequence with codons encoding alanine. While not wishing to be bound by theory, it is thought that incorporating an amino acid such as alanine, as opposed to other amino acids with larger side chains, in place of the cysteines normally found at those positions would result in less steric distortion of the resultant molecule. Those of skill in the art can easily determine other amino acid substitutions, including glycine, valine, leucine or alanine, which would also perform this function.

Figure 1:
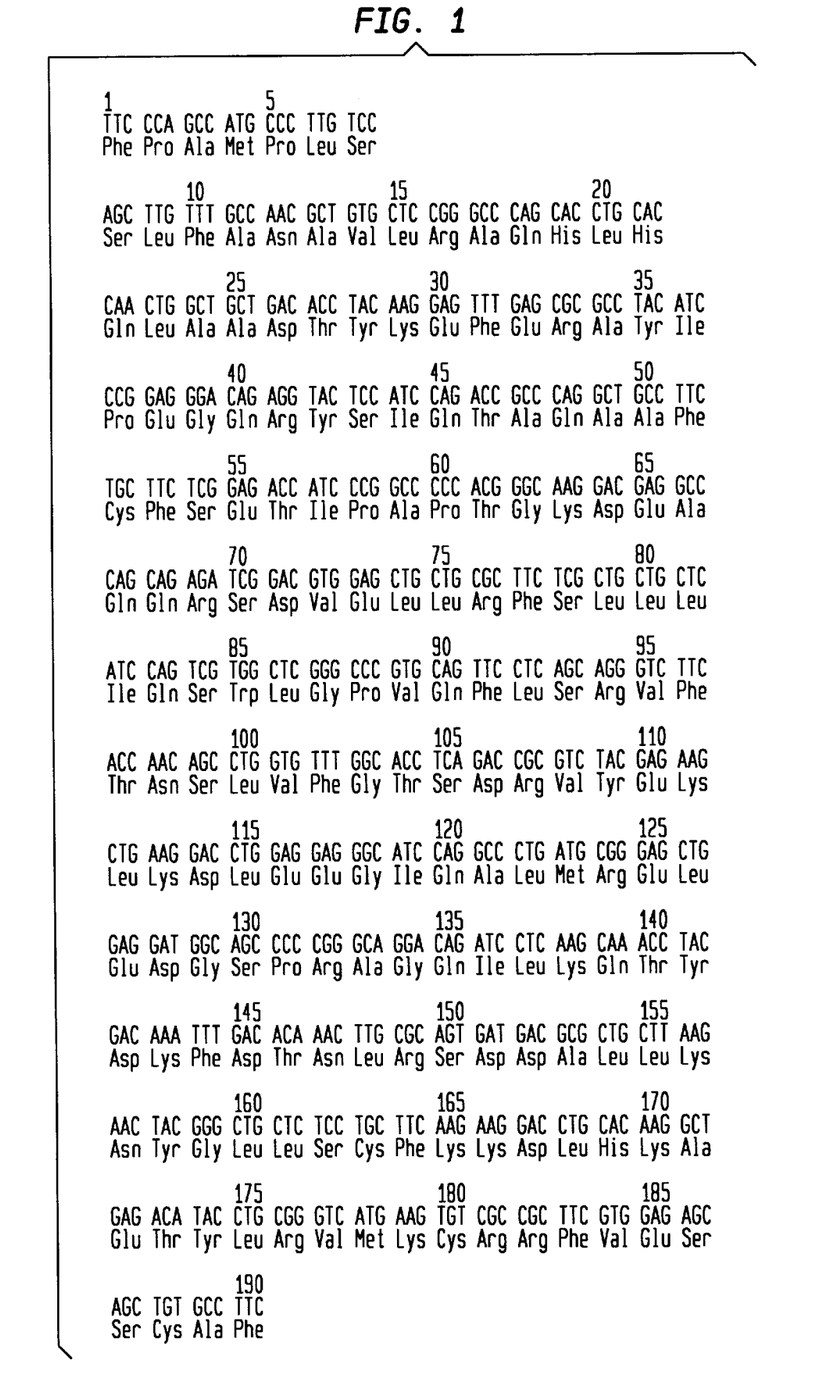
FIG. 1 is the nucleic and amino acid sequence of porcine somatotropin.
Figure 3:
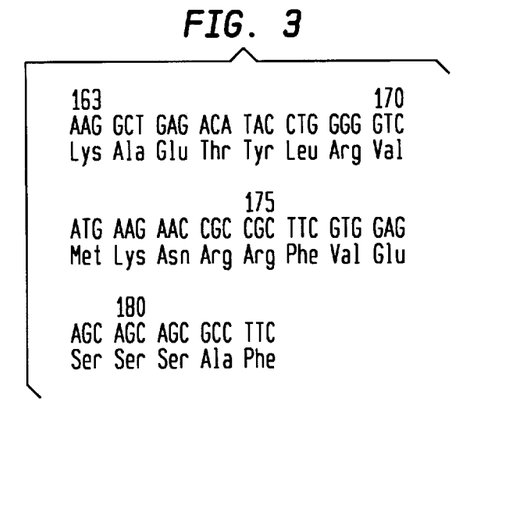
FIG. 3 is the nucleic and amino acid sequence of amino acids 163–183 of Δ7pST showing asparagine at position 173 and serine at position 181.

In an alternative embodiment of the present invention, shown in FIG. 3, the DNA sequence encoding Δ7pST has been modified by replacing the codons encoding cysteine at each of positions 173 and 181 in the amino acid sequence with nucleotides coding for asparagine at position 173 and serine at position 181. Again, while not wishing to be bound by theory it is thought that the hydrogen bonding between the amide group of asparagine and the hydroxyl group of serine would preserve the tertiary structure of the somatotropin while preventing intramolecular bonding. Other suitable amino acid substitutions can be determined by those of skill in the art and are intended to be encompassed within the scope of this invention.

To produce the modified DNA of the present invention by site-directed mutagenesis, a starting somatotropin DNA sequence is obtained. Methods for obtaining such DNA sequences are known to those of skill in the art. In general, the desired somatotropin gene is obtained from any suitable source and subcloned into an appropriate vector. Appropriate vectors are known to those skilled in the art and include phages, such as M13. The phage is grown in a mutant bacteria such as strains RZ1032 or CJ236, which are dut-ung-double mutant strains of *E. coli*. Such bacteria lack the enzyme dUTPase which results in high intracellular levels of dUTP and the enzyme uracil N-glycosylase which allows incorporated uracil to remain in the DNA. Single strands of these genes can be isolated and annealed and kinased to an oligonucleotide containing a desired nucleotide substitution. The oligonucleotide sequence preferably is complimentary to the corresponding sequence in the strand of foreign DNA present in the phage strand of the subclone including the replicating factor. This strand can be determined by locating the polylinker and the particular cloning sites used within the phage DNA sequence of the particular phage used. Such determinations can be easily performed by those of skill in the art and include, for example, reference to computer databases such as VECBASE, available through the University of Wisconsin. After determining the correct sequence, the oligonucleotide is synthesized and annealed to the single stranded DNA by methods known to those of skill in the art. The annealed oligonucleotide acts as a primer for complimentary strand synthesis using, for example, $T_4$ DNA polymerase. No dUTP is present in the reaction mixture while the complimentary strand is being synthesized in vitro. Thus, the complimentary strand will not contain uracil. After the entire complimentary strand is synthesized, ligation by, for example, $T_4$ DNA ligase, completes the construction of the double stranded gene. Next, selective pressure favoring the strand incorporating the oligonucleotide, i.e., not containing uracil, is applied by the method of Kunkel et al. incorporated hereby by reference.

Phages containing the appropriate alterations are detected by methods known to those of skill in the art. Such methods include, for example, restriction enzyme mapping or DNA sequencing.

The plasmids of the present invention contain the DNA coding for stable and bioactive small-loop modified somatotropins and the necessary elements required to express the somatotropin gene, including a promoter-operator region. Preferred plasmids are those which contain the DNA for small-loop modified porcine, bovine, or human somatotropin. Of these, a plasmid containing the DNA for small-loop modified porcine somatotropin is especially preferred.

Microorganism cells, and in particular bacterial cells, can be transformed with plasmids containing the desired DNA sequences coding for a small-loop modified somatotropin in accordance with conventional methods known to those of skill in the art. HB101 cells are particularly preferred. The microorganisms also can be cotransformed with other plasmids which facilitate the recovery of the somatotropin. Such other plasmids include plasmid pcI857 which contains a gene encoding a well-known temperature sensitive repressor protein. Such other plasmids do not constitute a portion of the present invention.

The recombinant cells of the present invention are cultivated and the somatotropin they produce is recovered. Both the cultivation and the recovery techniques are known to those of skill in the art and do not form a part of this invention.

The recovered somatotropin of the present invention has a bioactivity approximately equal to or greater than the bioactivity of a non-modified somatotropin.

Additionally, in the somatotropin of the present invention intramolecular cystine bonds are greatly reduced. Therefore, the somatotropin of the present invention remains in a bioactive form and is more stable during long term storage.

Another aspect of the invention provides for a pharmaceutical composition in which the modified somatotropin is combined with an acceptable carrier such as a diluent or other vehicle. The carrier can be any biocompatible, small-loop modified somatotropin compatible carrier, preferably phosphate buffered saline, tris-HCL, arginine, histidine, and the like. Generally, any biocompatible solution or carrier with a pH between 6 and 11 would function in the present invention as a carrier for the small-loop modified somatotropin. The small-loop modified somatotropin is mixed with the pharmaceutically acceptable carriers to form a composition which is stable during long term storage and allows for easy dosage preparation and administration. The composition preferably is lyophilized for storage.

Administration of the small-loop modified somatotropin to a target subject promotes growth in the target in a manner comparable to native somatotropins. Targets can be human or animal. Techniques of administering somatotropins are known to those of skill in the art. Such techniques are applicable to the administration of the pharmaceutical composition of the present invention.

The invention having been generally described, the following examples are given as particular embodiments of the invention and to demonstrate the practice and advantages thereof. These examples are for illustrative purposes only and they are not to be construed as limiting the scope of the invention. The recombinant porcine somatotropin (rpST) used in the examples below are produced using an *E. coli* microorganism on deposit with the American Type Culture Collection, Rockville, Md., having accession No. 53031. A complete description of the microorganism is given in U.S. Pat. No. 4,656,255, incorporated herein by reference.

EXAMPLES

1. Alteration of Cysteine 173 and Cysteine 181 by Site-Directed Oligonucleotide Mutagenesis a. Preparation of Competent JM103 cells.

JM103 cells were cultured overnight at 37° C. with a single colony from an M9 media plate. One hundred ml of warmed LB broth was inoculated with 1 ml of the overnight JM103 culture and incubated with shaking at 37° C. until an O.D.650=0.2 was reached. Then the culture was placed on ice for 20 minutes and centrifuged at 10,000 rpm for 10 minutes. The cell pellet was retained and washed with 50 ml of 100 mm of $MgCl_2$. This mixture again was centrifuged under the above described conditions and the supernatant again discarded. The cell pellet was suspended in 50 ml of 100 mM $CaCl_2$/50 mM $MgCl_2$ for one hour and pelleted as above. The cells were suspended in a storage solution of 1 ml chilled 100 mM $CaCl_2$/50 mM mg $Cl_2$/30% and stored in 0.2 ml aliquots at −80° C. until used.

b. Transformation of JM103 Cells With M13RF Delta-7-pST DNA

Three 0.2 ml aliquots of stored JM103 cells were slowly thawed in a bucket of ice. The cells were transformed via known procedures with 50 ng of M13RF Δ7pST DNA.

c. Incorporation of Uracil Into the M13 Template

A colorless plaque of the transformed cells was cored with a 200 ul capillary pipet from a plate and added to YT medium with an inoculum of strain JM103. This culture was grown overnight and centrifuged at 10,000 rpm for 10 minutes to pellet cells and cell debris. The M13mp11pST phage containing the pST gene was isolated from the JM103 culture and transfected into strain RZ1032 (dut⁻ung⁻). Growing the phage in strain RZ1032 (dut⁻ung⁻) ensured that uracil was incorporated into the phage DNA. Strain RZ1032 was grown in the presence of 20 ug/ml of tetracycline to maintain the amber suppressor phenotype. An overnight culture of this strain was inoculated into fresh LB broth and grown for 7–8 hours. Titrated phage stock of $10^{-6}$, $10^{-7}$ and $10^{-8}$ dilutions were mixed with this strain and allowed to absorb for 20 minutes. These cells containing the phage then were plated and an isolated plaque cored for an RZ1032 strain phage stock.

To isolate phage DNA containing uracil for use in the site-directed mutagenesis, the RZ1032 strain containing the M13mp11pST phage strain was grown in 500 ml of LB broth until an O.D.500=0.08. Then, 0.5 ml of the uracil-containing phage stock and uridine to a final concentration of 0.25 μg/ml were added. The resulting mixture was incubated for 6 hours with shaking at 37° C. The cells were pelleted and 7.25 g of NaCl and 12.5 g of PEG 8000 was added to the supernatant. The supernatant was placed on ice for 1 hour followed by centrifugation for 20 minutes at 10,000 rpm to pellet the phage. The phage then was banded in a CsCl gradient and dialyzed against TE buffer. The single-stranded DNA from the phage was extracted by addition of an equal volume of phenol:chloroform (1:1), vortexed and centrifuged to separate the two phases. The aqueous phase containing the phage DNA was reextracted with phenol two times, followed by dialysis against additional TE buffer.

Oligonucleotides for the site-directed mutagenesis were synthesized and HPLC purified at the University of Illinois, Genetic Engineering Laboratory, Urbana, Ill. The mutagenic oligonucleotides were constructed such that the altered codon was flanked by 3 codons on each side. 200 pmoles of the 21mer oligonucleotide were first kinased. A molar ratio of 30:1 oligonucleotide to template was used for the annealing reaction. Annealing was done by heating the reaction mix to 70° C. and allowing the reaction to cool to 30° C. at a rate of 1° C./min. After cooling, complementary strand synthesis buffer, obtainable from Bio-Rad, 5 units of T4 DNA ligase, 2 ug of gene 32 protein (1 unit), 1 unit of T4 DNA polymerase were added to the tube in the order listed. The reaction mix was placed on ice for 5 minutes, followed by 5 minutes at room temperature and finally the reaction mix was placed in a water bath at 37° C. for 90 minutes. The reaction was stopped with the addition of TE buffer and used to transform JM103 strain competent cells. These transformed cells were mixed with a logarithmically growing culture of strain JM103 and plated in LB top agar. Plaques were cored and placed in buffer. This phage stock was used to inoculate a JM103 culture which was grown overnight and used for a plasmid minipreparation. The alkaline lysis method described by Maniatis was used for the plasmic minipreparation isolation. An initial identification of the correct mutation was done using restriction enzyme analysis. Alteration of the codon for cysteine to a codon for asparagine at position 173 created an additional Mbo II restriction enzyme site. This was visualized by restriction enzyme digestion of plasmid DNA. After the initial identification of this first codon change, the altered DNA was retransformed into the RZ1032 strain, DNA isolated and a second site-directed mutagenesis performed to alter the codon for the cysteine at position 181 to a codon for serine.

Alteration of this codon eliminated a Pvu II restriction enzyme site. This was also visualized by restriction enzyme digestion of plasmid DNA. Definitive confirmation of these alterations was by DNA sequencing. DNA incorporating these mutations then was placed into a pIC101 expression vector. Both mutant RF DNA and plasmid pIC101 were restriction enzyme digested with BstX I and BamH I. The 366 bp BstX I and BamH I DNA fragment containing the mutated region was ligated into plasmid pIC101 replacing the wild type region. This new plasmid containing the asn(173) ser(181) modification was named pPM100. *E. coli* HB101 containing this plasmid and plasmid pcI857 have been deposited with the ATTC and granted accession number 68226.

2. Verification of the Alteration of the pST Gene

After identification of a potential mutant by altered restriction enzyme analysis, confirmation was by DNA sequencing analysis. The DNA sequencing method used was a modification of the Promega pGEM system (Promega Biotec, 2800 S. Fish Hatchery Rd., Madison, Wis. 53711–5305) which involves denaturing a double stranded molecule for use as the template. Cesium chloride purified mutant RF DNA was used for the DNA sequencing. A 17mer oligonucleotide which was homologous to a region of the DNA which was upstream from the mutated region was synthesized as a DNA sequencing primer.

3. Recovery of Monomer Protein

Recovery of porcine somatotropin (pST) from the bacterial strain containing plasmid pPM100 was characterized by a significant reduction in the high molecular weight protein to monomer ratio which can be reduced as much as 50% and an increase in yield of recoverable protein. This reduction in high molecular weight protein in addition to the positive effect on yield also allows for ease of processing. Recovery of modified protein was as much as 182% of unmodified protein. Recovery and purification of porcine somatotropin was by the method previously described by Rausch and Meng and incorporated herein by reference.

Figure 7:
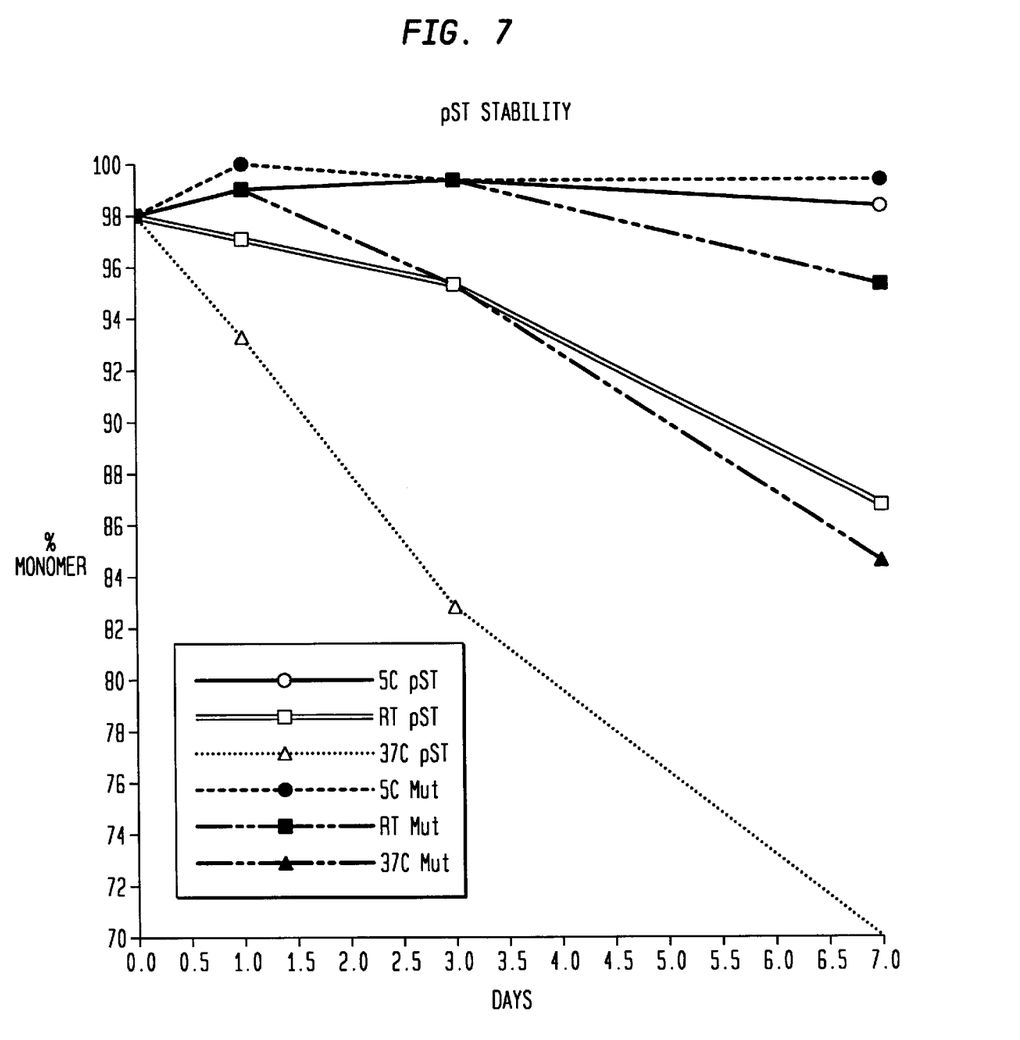
FIG. 7 compares the percent monomer remaining after a number of days for modified pST according to the present invention with a native pST.

The modified pST displayed an increased stability during storage in solution. The purified somatotropin, when dissolved in various buffers at various temperatures, demonstrated an increased stability and resistance to aggregation and degradation in solution. When compared to the unmodified protein, the modified protein showed as much as a 20% increase in the amount of monomeric pST remaining in solution after 7 days. These data demonstrate increased stability of the modified pST protein, as reflected in FIG. 7.

4. Verification of Production of an Altered Protein 10 mg of the modified asn(173) ser(181)Δ7pST was digested with cyanogen bromide to cleave the protein at the methionine residues within the protein. This, without reduction of the large loop, resulted in two peptides of different sizes. The small 12 amino acid C-terminal peptide was isolated by size exclusion chromatography using a Beckman Spherogel TSK SW300 column. The mobile phase for the size exclusion chromatography was 1% formic acid. After isolation of the C-terminal peptide by chromatography, the peptide was characterized as to amino acid sequence with an Applied Biosystems 477A protein sequencer. This sequencer was operated according to manufacturers recommendations.

The 12 amino acid C-terminal peptide amino was experimentally determined to be Lys-Asn-Arg-Arg-Phe-Val-Glu-Ser-Ser-Ser-Ala-Phe. This sequence was in agreement with the predicted sequence for the modified protein and verifies the changes of cysteine 173 to asparagine and cysteine 181 to serine.

5. Radioreceptor Assay

A radioreceptor assay (RRA) was used to measure directly the binding of the pST molecules to their cell surface receptors. The methodology used was a modification of that originally described by Tsushima and Friesen, Radioreceptor Assay for Growth Hormone, J. Clin. Endocrinol. Metab., 37:334–337 (1973). Pregnant rabbit liver microsomes have been shown by Gerasimo et al. (1979) to contain a marked increase in somatotropin binding protein. Consequently, these were used in the assay. Further optimization and characterization of this assay for porcine somatotropin has been described by Chung and Etherton (1986). Samples of 1 mg/ml of modified Δ7pST were prepared and labelled with I 125. Unmodified laboratory standard Δ7pST was used as a control and used for the estimation of binding activity. A four-parameter logistic equation was used for data analysis. The four parameters were calculated for each displacement curve using ALLFIT (Delean et al., 1977). The modified asn(173) ser(181)Δ7pST molecule in two separate assays had 190% and 225% binding activity of the control.

6. Protein Stability

Figure 8:
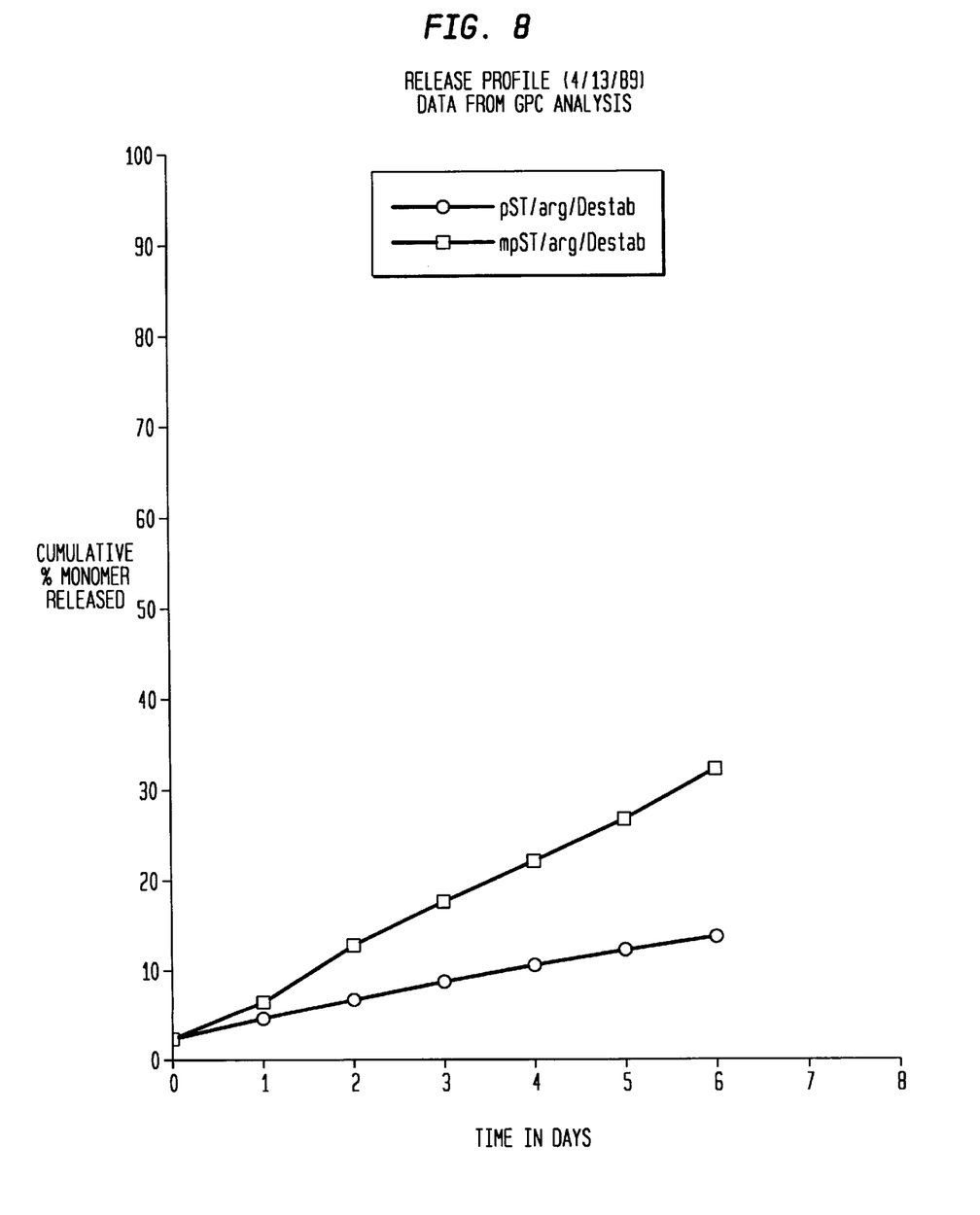
FIG. 8 illustrates the release profile of modified and native porcine somatotropin from a controlled release implant.

Formulations of modified Δ7pST or Δ7pST (1 part by weight) with L-arginine, free base (3 parts), and Destab, a directly compressible form of sucrose (1 part) were blended and compressed using a Key International single punch press to yield 100 mg pellets measuring 4 mm in diameter. Three pellets were inserted into pre-cut silicon tubing which was sealed to one end of the tubing with glass beads. A microporous polyethylene disc was inserted into the other end. These implants were placed in 10 mM phosphate buffered saline (pH: 7.4) with the solutions changed and analyzed daily. Analysis of these solutions by FPLC indicated that in the implants containing pST, 17% of monomeric protein had been released after 7 days. The formulation containing the modified pST released 37% of monomer during the same time period. These data indicate that under alkaline conditions, the modified pST decreases aggregation and increases the amount of bioactive protein released and are illustrated in FIG. 8.

We claim:

1. A stable and bioactive somatotropin pharmaceutical composition comprising a small-loop modified Δ7 porcine somatotropin, and a pharmaceutically acceptable carrier therefor, wherein said somatotropin is Δ7 psT asn (173) ser (181).

2. The pharmaceutical composition of claim 1 wherein said composition is lyophilized.

3. A method for promoting growth in a human or animal comprising administering to said human or animal a growth promoting amount of the pharmaceutical composition of claim 1.

4. A Δ7 porcine somatotropin having the amino acid sequence encoded for by the following DNA sequence:

```
  1                      5                          10
AGC TTG TTT GCC AAC GCT GTG CTC CGG GCC CAG CAC CTG CAC
Ser Leu Phe Ala Asn Ala Val Leu Arg Ala Gln His Leu His 15                          20                         25
CAA CTG GCT GCT GAC ACC TAC AAG GAG TTT GAG CGC GCC TAC ATC
Gln Leu Ala Ala Asp Thr Tyr Lys Glu Phe Glu Arg Ala Tyr Ile 30                          35                         40
CCG GAG GGA CAG AGG TAC TCC ATC CAG ACC GCC CAG GCT GCC TTC
Pro Glu Gly Gln Arg Tyr Ser Ile Gln Thr Ala Gln Ala Ala Phe 45                          50                         55
TGC TTC TCG GAG ACC ATC CCG GCC CCC ACG CCG AAG GAC GAG GCC
Cys Phe Ser Glu Thr Ile Pro Ala Pro Thr Gly Lys Asp Glu Ala 60                          65                         70
CAG CAG AGA TCG GAC GTG GAG CTG CTG CGC TTC TCG CTG CTG CTC
Gln Gln Arg Ser Asp Val Glu Leu Leu Arg Phe Ser Leu Leu Leu 75                          80                         85
ATC CAG TCG TGG CTC GGG CCC GTG CAG TTC CTC AGC AGG GTC TTC
Ile Gln Ser Trp Leu Gly Pro Val Gln Phe Leu Ser Arg Val Phe 90                          95                        100
ACC AAC AGC CTG GTG TTT GGC ACC TCA GAC CGC GTC TAC GAG AAG
Thr Asn Ser Leu Val Phe Gly Thr Ser Asp Arg Val Tyr Glu Lys 105                         110                        115
CTG AAG GAC CTG GAG GAG GGC ATC CAG GCC CTG ATG CGG GAG CTG
Leu Lys Asp Leu Glu Glu Gly Ile Gln Ala Leu Met Arg Glu Leu 120                         125                        130
GAG GAT GGC AGC CCC CGG GCA GGA CAG ATC CTC AAG CAA ACC TAC
Glu Asp Gly Ser Pro Arg Ala Gly Gln Ile Leu Lys Gln Thr Tyr 135                         140                        145
GAC AAA TTT GAC ACA AAC TTG CGC AGT GAT GAC GCG CTG CTT AAG
Asp Lys Phe Asp Thr Asn Leu Arg Ser Asp Asp Ala Leu Leu Lys 150                         155                        160
AAC TAC GGG CTG CTC TCC TGC TTC AAG AAG GAC CTG CAC AAG GCT
Asn Tyr Gly Leu Leu Ser Cys Phe Lys Lys Asp Leu His Lys Ala 165                         170                        175
GAG ACA TAC CTG CGG GTC ATG AAG AAC CGC CGC TTC GTG GAG AGC
Glu Thr Tyr Leu Arg Val Met Lys Asn Arg Arg Phe Val Glu Ser

180
AGC TCC GCC TTC
Ser Ser Ala Phe.
```

\* \* \* \* \*